United States Patent
Bhandari et al.

(10) Patent No.: US 11,589,783 B2
(45) Date of Patent: Feb. 28, 2023

(54) APPARATUS AND METHOD FOR DIAGNOSING VERTIGO AND BALANCE RELATED AILMENT

(71) Applicant: Rajneesh Bhandari, Jaipur (IN)

(72) Inventors: Rajneesh Bhandari, Jaipur (IN); Anita Bhandari, Jaipur (IN)

(*) Notice: Subject to any disclaimer, the term of this patent is extended or adjusted under 35 U.S.C. 154(b) by 1267 days.

(21) Appl. No.: 15/575,385

(22) PCT Filed: Sep. 4, 2015

(86) PCT No.: PCT/IB2015/056759
§ 371 (c)(1),
(2) Date: Nov. 20, 2017

(87) PCT Pub. No.: WO2016/189365
PCT Pub. Date: Dec. 1, 2016

(65) Prior Publication Data
US 2020/0113492 A1    Apr. 16, 2020

(30) Foreign Application Priority Data
May 26, 2015   (IN) .............. 1502/DEL/2015

(51) Int. Cl.
*A61B 5/11* (2006.01)
*A61B 5/00* (2006.01)

(52) U.S. Cl.
CPC .......... *A61B 5/1128* (2013.01); *A61B 5/6803* (2013.01)

(58) Field of Classification Search
CPC .............. A61B 5/1128; A61B 5/6803
See application file for complete search history.

(56) References Cited

U.S. PATENT DOCUMENTS

| | | | |
|---|---|---|---|
| 5,086,404 A * | 2/1992 | Claussen | A61B 5/1114 348/121 |
| 5,871,271 A * | 2/1999 | Chien | A42B 3/044 362/800 |
| 2002/0116990 A1 * | 8/2002 | Claussen | A61B 5/1121 73/65.01 |

\* cited by examiner

*Primary Examiner* — Alex M Valvis
*Assistant Examiner* — Yasmeen S Warsi
(74) *Attorney, Agent, or Firm* — United IP Counselors, LLC

(57) ABSTRACT

Disclosed is an apparatus for diagnosing vertigo and balance related ailment using Craniocorpography (CCG) technique. The apparatus includes a helmet adapted to be worn over a head of a patient. The helmet includes a plurality of light emitting diodes (LEDs). Further, the apparatus includes a camera placed directionally above at a vertical distance from the helmet while the helmet is being worn over the head of the patient. The camera is adapted to track movement of the patient when the CCG is performed on the patient. Furthermore, the apparatus includes an interface card adapted to connect the camera. The interface card is adapted to relay images captured by the camera. A computing system in communication with the interface card is also provided. The computing system is adapted to analyze and present at least a plurality of patient alignment parameters based on the images captured by the camera.

19 Claims, 14 Drawing Sheets

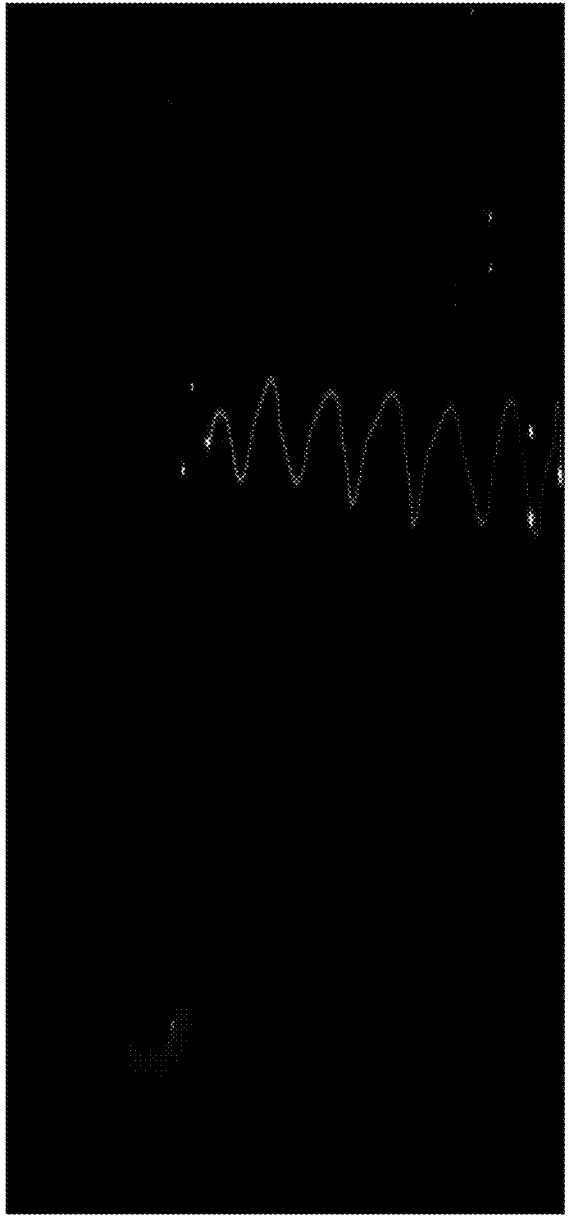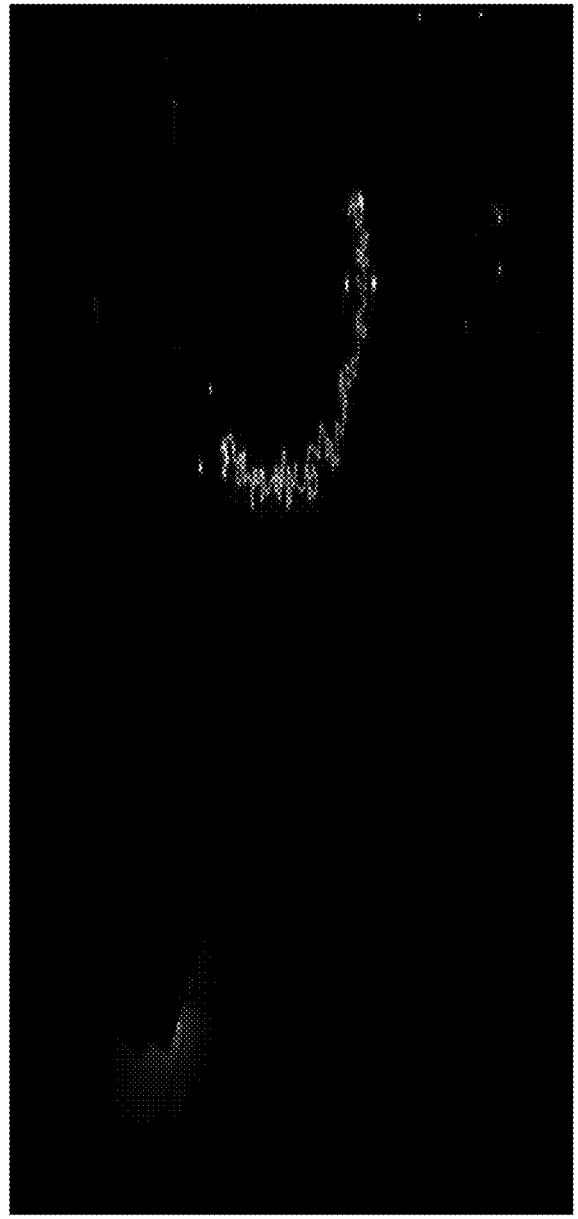
Fig. 7                    Fig. 8

TANDEM WALKING TEST
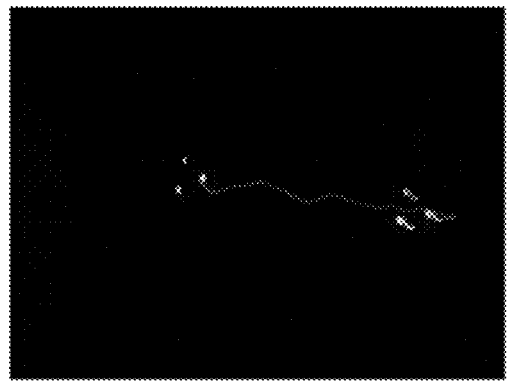
UNTER BURGER'S TEST
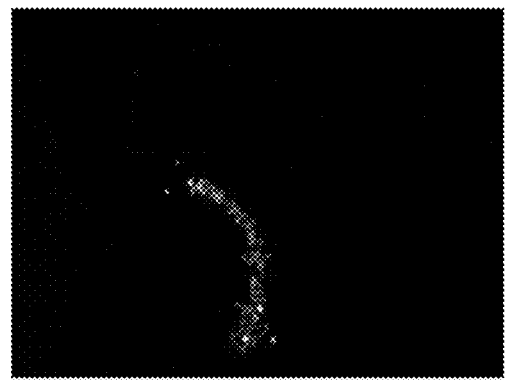
| Displacemen | 99 | Sway (cm) | 9 | Angle of Dev. | Right : 46 |
| Body Axis | Right : 133 | Exposure | 99 | | |
DISPLACEMENT
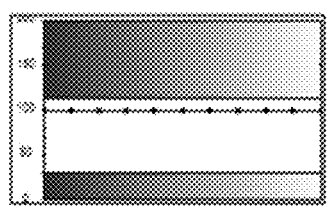
Displacement
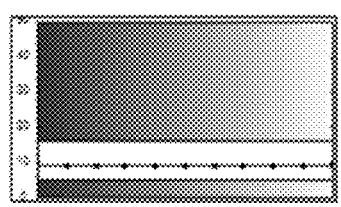
Sway
ANGLE
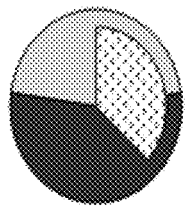
Body Axis Spin
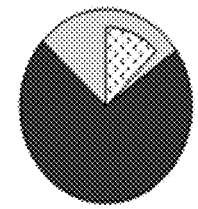
Angular Deviation
Fig. 13

APPARATUS AND METHOD FOR DIAGNOSING VERTIGO AND BALANCE RELATED AILMENT

FIELD OF THE DISCLOSURE

The present invention relates to the field of diagnosing vertigo and balance related ailments of a human being, and more particularly, the present invention provides an apparatus and method for diagnosing vertigo and balance related ailments.

BACKGROUND OF THE DISCLOSURE

To maintain balance and equilibrium, the human body is dependent on three systems named as 1) Vestibulocular reflex, 2) Vestibulospinal reflex, and 3) Vestibulocollic reflex. The vestibulospinal reflex works through the sensations collected from the joints and muscles of the human body. These collected sensations are transmitted through the spinal cord to the vestibular nerve and finally reaches the central nervous system in the brain. Craniocorpography is a test to evaluate the vestibulospinal system.

Human body balance is related to the healthy functioning of the human equilibrium system. As per scientific literature, 40% of the population will suffer from vertigo and balance related problems at some stage of their life. The disorders of human equilibrium system have various symptoms but few measurable signs. Accordingly, there is always a demand for a system adapted to measure various sign and symptoms related to the human equilibrium disorders.

Many medical professional have studied the human equilibrium in relation to the vestibular system and its central pathways. In 1938, Unterberger's stepping test was proposed which was later modified by Japanese otolaryngologist Fukuda. In 1968, a German neurootologist Claus-Frenz Claussen developed a method in which movement of the patient during Unterberger's stepping test is photographed and named it Craniocorpography. FIGS. 1-3 provide various apparatuses and test for diagnosing balance related disorders specially for evaluation of the vestibulospinal reflex which may be deranged in vertigo & balance related disorders.

Accordingly, Craniocorpography is a diagnostic test adapted to measure the various sign and symptoms of the human equilibrium disorders. During Craniocorpography gait testing is done and the movement images of the patient are captured and recorded. Based on the captured images, the stance and gait of the patient are measured. In Craniocorpography recording, three tests are evaluated i.e. Romberg test, Tandem walking and Unterberg's test. The Unterberg test is performed by asking the patient to stand with arms stretched out and eyes closed and then the patient is asked to take a predetermined number of steps on the spot. In case the patient is suffering from balance related ailments, he/she moves from his/her original position much more than a normal patient. The Craniocorpography test is usually performed in a quiet dark room and at least four parameters of the body movement pattern are measured i.e. linear displacement, sway, angular rotation, and body axis spin. Romberg test involves asking the patient to stand in one place with arms stretched out and eyes closed. In tandem walking, the subject is asked to walk in a straight line with eyes closed.

In another similar method which is variation of Craniocorpography test, a cross is drawn on the floor and the sideward deviation of the patient is measured. The disadvantage of this method was that only starting and final position of the patient is measured due to which only deviation and rotation of the patient could be measured.

In yet another similar method which is another variation of Craniocorpography test, some light sources are placed over the head and the shoulder of the patient and then the light tracings of head and shoulder movements are captured by camera and developed into photographs. In this test method, a helmet having two bulbs fitted in sagittal axis is worn by the patient, wherein, an anterior bulb is positioned at the forehead and a posterior bulb is positioned at an occiput position of the helmet, as shown with reference to FIG. 1. Further, there are two other bulbs fitted on the shoulders of the patient to measure a coronal axis tracing.

FIG. 1 illustrates the traditional apparatus and the method for conducting a Craniocorpography test, where, patient (100) is asked to wear a helmet (101) over his/her head and then step on the spot in a test room (500) for a predetermined number of steps, usually about ninety steps.

Further, a camera (200) is placed on a stand (420) having its lens directed upwards towards a convex mirror (300) fitted on ceiling of the test room (500). The convex mirror (300) condenses and reflects the incident image of the patient (100) while the Craniocorpography test is being performed on the patient (100), onto the camera (200) lens. The camera (200) is placed on bulb setting which remains on during the test and captures the whole movement of the patient (100) during the test procedure. The patient (100) is usually blindfolded during the test. The picture taken by the camera (200) is developed and manual calculations are done based on the captured images of the camera (200). Usually, the whole assembly is driven by a battery contained in the helmet (101). All the bulbs blink at three second intervals. This test is done in a dark and sound proof test room (500) to avoid all cues.

To simplify the recording procedure of Craniocorpography, a modification was introduced by Dr. M. V. Kirtane in the test. The modification is as shown with reference to FIG. 2.

In this modification, a head band (1000), a mirror, a ruler (500), and three lights (104 & 105) are used. The light (105) in center of the head band (1000) is the main recording light, while the other two lights (104) which are placed forty centimeters apart from each other on the ruler (500) act as a scale to compare the patient's movements.

In this arrangement there is no need for using the shoulder lights, as in the first test. This test is done in a dark room. The initial position of the patient (100) is recorded with all three lights on. After that, the two lights (104) placed on the ruler (500) are switched off and the patient is made to carry out Romberg test, tandem walking test and Unterburger test. At the end of the test, all three lights (104, 105) are switched on and the final position of the patient (100) is recorded.

In another development, an ultrasound computerized Craniocorpography test is developed, in which evaluation is done by run time differences of ultrasound impulses between sender and receivers by local positioning systems.

In this test, the patient is made to wear a helmet with two ultrasound markers and two shoulder suspenders with two other ultrasound markers. A computer triggers the ultrasound impulses. Behind and above the patient are several ultrasound receivers with microphones and data processors. The signals are sent to the computer unit for calculation of spatial position. During the recording, each marker is producing a short sound impulse. The sound impulses are received by the three microphones. The signals are received, processed and transmitted to a computing system. The run time difference of each acoustic marker is analyzed to form a spatial image of all the markers. In this technique, patient is blindfolded.

Accordingly, there are various types of devices and methods adapted to perform the Craniocorpography test on a human being. However, these known devices and methods have some drawbacks. These drawbacks are as follows.

In traditional Craniocorpography tests, a convex mirror is used to record the movement of patient. Usually, a significant disadvantage of the convex mirror is that it distorts distances, which are to be measured. Secondly, all these tests are manual. Usually, after the tests are performed, the photographs are printed, manual calculations are done based on the printed photographs to find the four test parameters.

Thirdly, the time taken to produce the report is at least a few hours to a few days. Moreover, as the height of patient changes, the distance between the convex mirror and the patient head, varies and consequently the distance measurement changes. Further, in the traditional Craniocorpography tests as explained above, a separate stopwatch is required to find the time taken to complete ninety test steps. On the other hand, most of the tests, such as the advanced ultrasound Craniocorpography is a very expensive test as it involves expensive equipment.

Hence, there is a need to develop a simple, efficient and cost effective apparatus which can efficiently measure and track the gait of the subject in different situations by cutting off visual, tactile and proprioceptive cues and can also solve the aforesaid limitations of traditional Craniocorpography test equipment.

Therefore, an object of the present invention is to create an apparatus adapted to quickly and accurately measure the sign and symptoms of the human equilibrium disorders.

Another objective of the present invention is to accurately measure and track the gait of the patient without giving visual or proprioceptive cues to find out how the vestibulospinal system is functioning.

Another objective of the present invention is to build very simple and patient friendly diagnostic apparatus to be used by many individuals having different body structure.

Yet another object of the present invention is to produce the outcome and report of the Craniocorpography test as quickly as possible, with limited manual interference.

Yet another object of the present invention is to provide a simple and accurate Craniocorpography test procedure to be implemented without any complexity.

Yet another object of the present invention is to provide a simple Craniocorpography test procedure, which is inexpensive.

Yet another object of the present invention is to provide a diagnostic apparatus adapted to be used in a variety of conditions such as in a dark room as well as in a light room.

These and other objects and advantages of the invention will be clear from the ensuing description.

SUMMARY

In view of the aforesaid needs and shortcomings in the state of the art, in an aspect, the present invention provides an apparatus for diagnosing the vertigo and balance related ailments of the human being.

The apparatus includes a helmet adapted to be worn over a head of the patient. The helmet includes a plurality of light emitting diodes. Further, the present apparatus includes a camera placed directionally above at a vertical distance from the helmet while the helmet is being worn over the head of the patient. The camera is adapted to track movement of the patient when the Craniocorpography technique is being performed on the patient.

Further, the apparatus includes an interface card adapted to connect the camera. The interface card adapted to relay images captured by the camera. Furthermore, the apparatus includes a computing system in communication with the interface card. The computing system is adapted to compute a plurality of patient alignment parameters processed based on the images captured by the camera. The plurality of patient alignment parameters used for diagnosing vertigo and balance related ailment.

In one embodiment, the apparatus includes a controller coupled to the camera, wherein the controller is adapted to control the camera.

Furthermore, in another aspect, the present invention provides a method for diagnosing vertigo and balance related ailment of the patient by using Craniocorpography technique. The method includes placing a helmet over a head of a patient. The helmet includes a plurality of light emitting diodes. The next step involves capturing images of the patient through a camera when the Craniocorpography technique is being performed on the patient. The camera is placed directionally above at a vertical distance from the helmet when being worn over the head of the patient.

The next step involves transferring the said captured movement images of the patient from the camera to a computing device. The transferring of said captured movement images is done through an interface card which is coupled to the camera. In the next step, the said captured movement images are analyzed and processed through the computing device. In the next step, a plurality of patient alignment parameters is determined by using a processing program of the computing device. In the next step, the said determined patient alignment parameters are presented through the computing device. The patient alignment parameters are useful for diagnosing vertigo and balance related ailment.

In one embodiment, the method includes controlling functionality of the camera via a remote control device. In another embodiment, the method includes controlling the direction of the camera by the controller.

These aspects together with other aspects of the present invention, along with the various features of novelty that characterize the present invention, are pointed out with particularity in the claims annexed hereto and form a part of this present invention. For a better understanding of the present invention, its operating advantages, and the specific objects attained by its uses, reference should be made to the accompanying drawing and descriptive matter in which there is illustrated an exemplary embodiment of the present invention.

DESCRIPTION OF THE DRAWINGS

The advantages and features of the present invention will become better understood with reference to the following detailed description taken in conjunction with the accompanying drawings, in which:

FIG. 7 illustrates a test result for the increased sway of the patient, using the apparatus of the present invention, according to various embodiments of the present invention;

FIG. 8 illustrates a test result showing angular deviation of the patient to the left side, using the apparatus of the present invention, according to various embodiments of the present invention;

FIGS. 12-16 illustrate a plurality of exemplary test reports automatically generated by the apparatus, according to various embodiments of the present invention.

Like reference numerals refer to like parts throughout the description of several views of the drawing.

DESCRIPTION OF THE INVENTION

Figure 1:
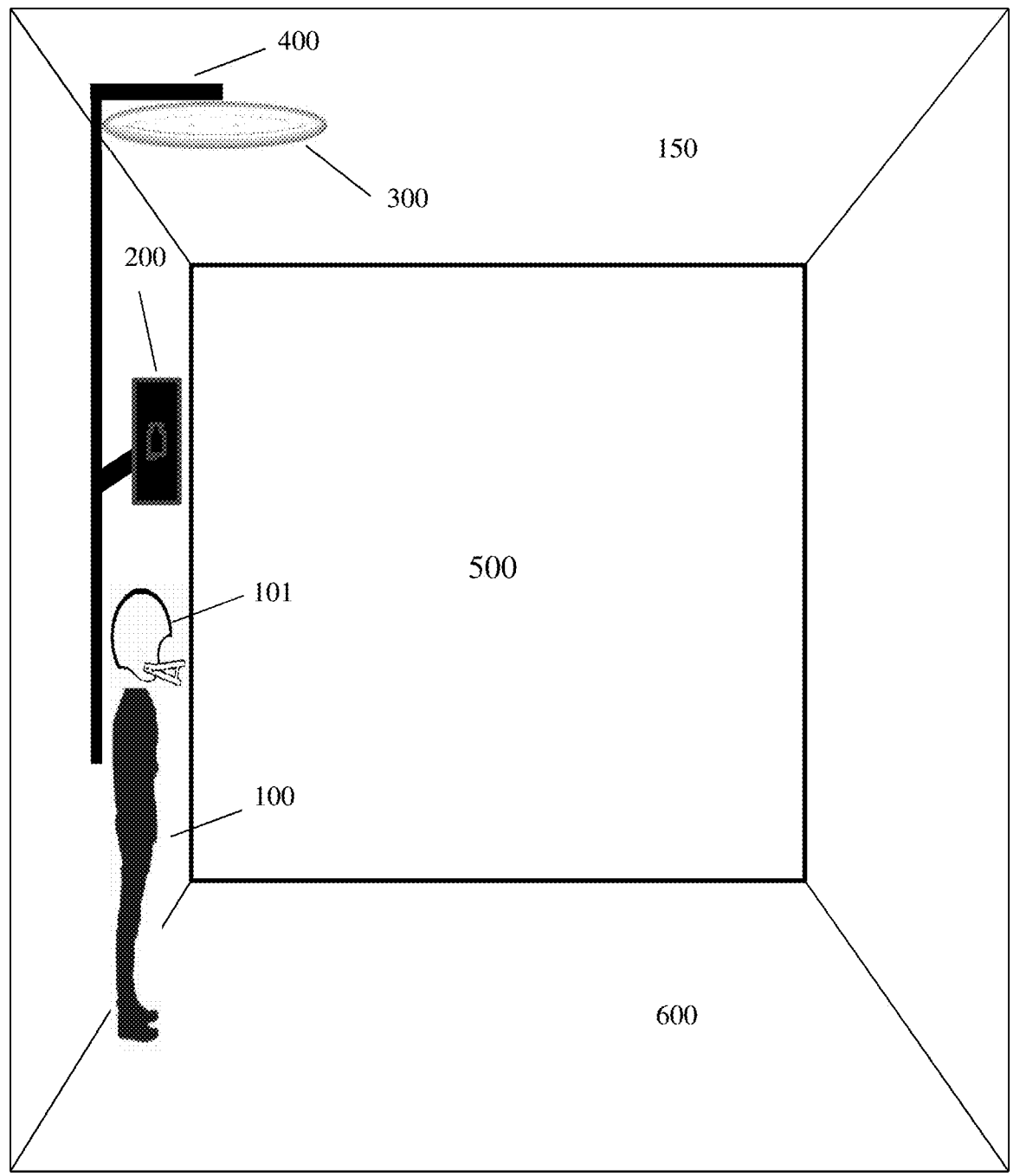
FIG. 1 illustrates a traditional method for evaluating the human balance and vertigo disorders and performing a Craniocorpography (CCG) test by using a convex mirror.
Figure 2:
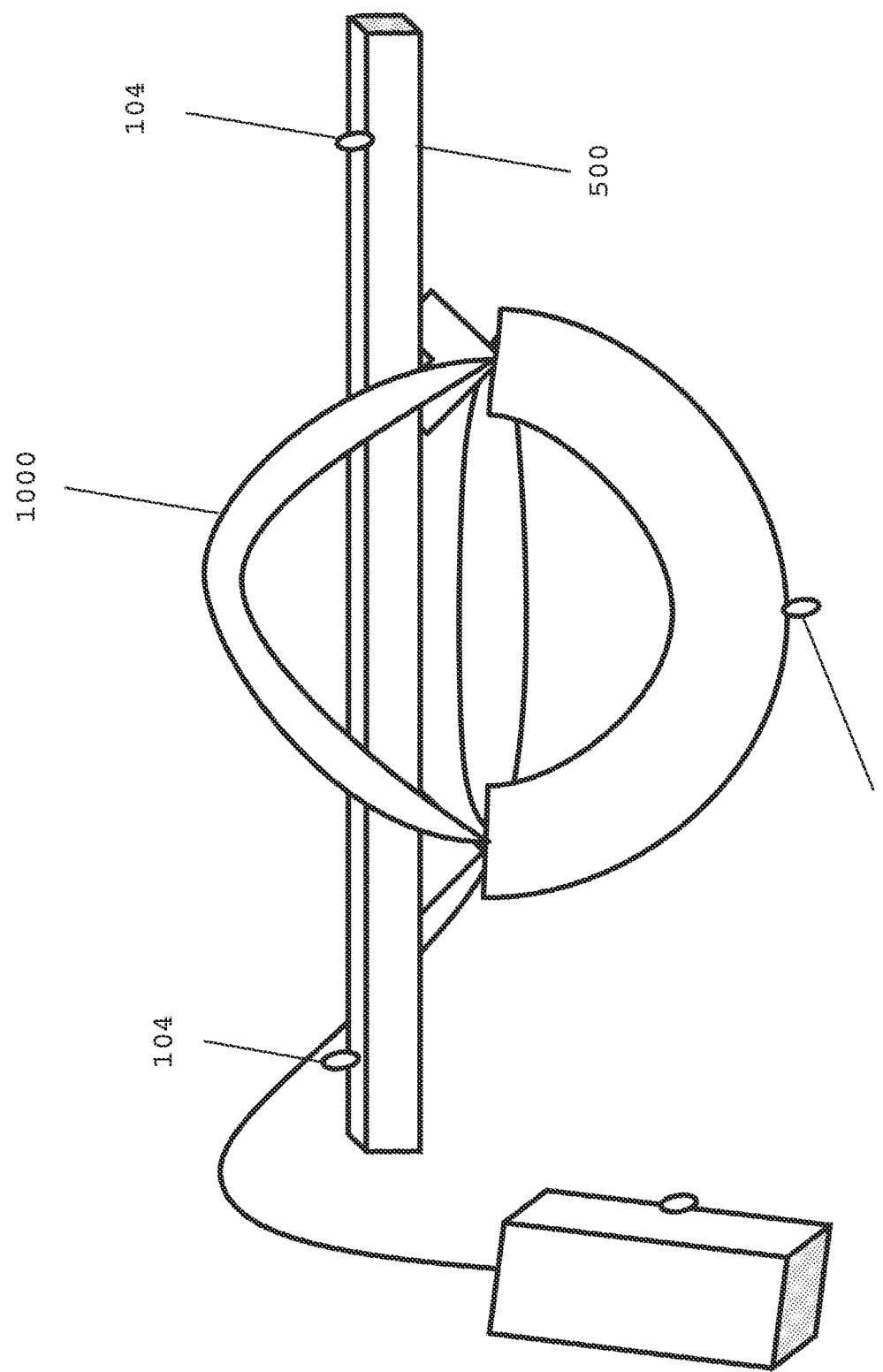
FIG. 2 illustrates another traditional method for evaluating human balance and vertigo disorders by performing a Craniocorpography (CCG) test by using a head band and a light rod.

The exemplary embodiments described herein detail for illustrative purposes are subjected to many variations. It should be emphasized, however, that the present invention is not limited to device and method only for measuring the movement images of a subject. It is understood that various omissions and substitutions of equivalents are contemplated as circumstances may suggest or render expedient, but these are intended to cover the application or implementation without departing from the spirit or scope of the present invention.

The terms "a" and "an" herein do not denote a limitation of quantity, but rather denote the presence of at least one of the referenced item.

The terms "having", "comprising", "including", and variations thereof signify the presence of a component.

The term "test" refers to the Craniocorpography test or interchangeably called as CCG test.

The term "test steps" usually refers to the act where the patient is asked to take 90 steps on the spot, in an open room (lit or dark). It will be apparent to a person skilled in the art that if the patient has balance disorders, such act will lead to non-intentional movement of the patient.

The balance of a person is largely controlled by three reflexes such as vestibuloocular reflex, vestibulospinal reflex and vestibulocollic reflex. The vestibulocular reflex is mainly assessed by videonystagmography. The vestibulospinal reflex is studied through body movement patterns. The vestibulocollic reflex is usually evaluated by vestibular evoked myogenic potentials [VEMP] and subjective visual vertical tests.

Accordingly, there are number of evaluation test, procedure and apparatus required to determine the balance and vertigo disorders of the patient. Accordingly, there is a need to develop a simple, efficient and cost effective apparatus and Craniocorpography (CCG) test which can efficiently measure the sign and symptoms of the human equilibrium disorders. The present invention provides an apparatus adapted to make Craniocorpography a simple, repeatable and accurate test for vertiginous patients.

The present invention provides a very simple and reliable apparatus for conducting Craniocorpography test or interchangeably called as CCG test, throughout the description. Broadly speaking, the present apparatus comprises a helmet adapted to be worn over a head of the patient. Further, the present apparatus also includes a camera, a computing system operatively connected with the said camera, and a controller adapted to control the camera, and an interface card adapted to connect the camera with the computing system.

The said helmet includes a plurality of light sources, such as light emitting diodes (interchangeably called "LEDs" or "LED") implanted thereon in such a manner that they provide a light source for detecting the patient movement in the dark room. The plurality of light emitting diodes includes at least three blue light emitting diodes and at least one red light emitting diode. In one embodiment, the helmet includes 3 blue LEDs and one red LED.

In one embodiment, the at least three blue light-emitting diodes are configured on an equal distance from each other. The at least one red light emitting diode is configured adjacent to one of the three blue light-emitting diodes.

The apparatus is designed in such a way that the at least three blue light-emitting diodes are turned on at a starting point and at a final point while performing the Craniocorpography test on the patient. Whereas, the at least one red light-emitting diode remains turned on throughout the operation of the Craniocorpography test being performed on the patient. The at least one red light-emitting diode provides a means of showing a movement path of the patient.

In one embodiment, the camera placed above is adapted to capture the movement images of the patient. The camera may be remotely controlled by a controller. The controlling function may be related to shutter operation, direction of the camera, pan, zoom, or any other relevant operation of the camera.

The Interface card of present apparatus is adapted to connect the camera with the computing system. The said captured movement images of the patient are transferred from the camera to the computing device via the interface card. The said captured movement images of the patient are analyzed through the computing device.

The said captured movement images of the patient are processed through a data processing program. Accordingly, the present invention provides an easy way for automatically determining a plurality of patient alignment parameters such as longitudinal displacement of the patient, sway of the patient, angular deviation of the patient, body axis spin of the patient and stepping time of the patient.

Figure 3:
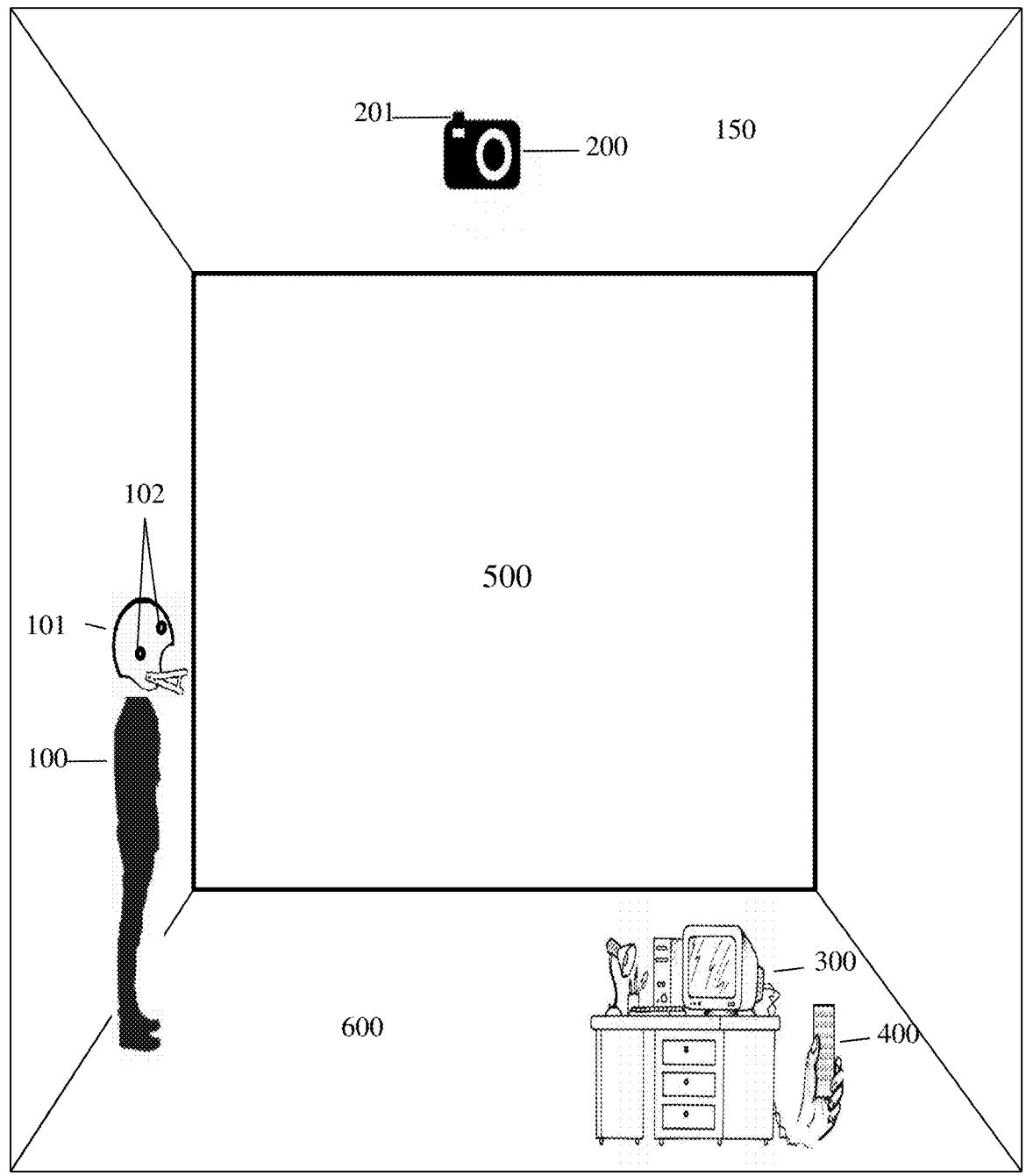
FIG. 3 illustrates arrangement of various parts of apparatus for performing a Craniocorpography (CCG) test, according to various embodiments of the present invention.
Figure 4:
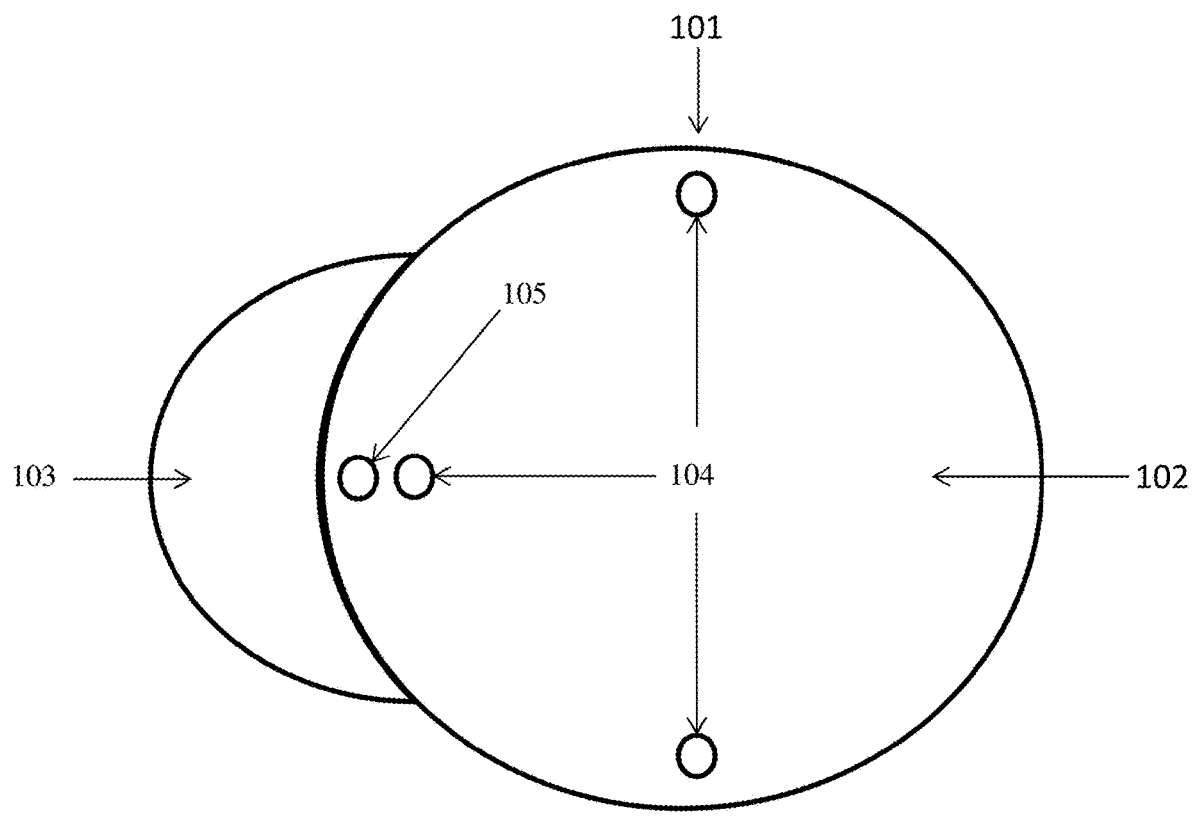
FIG. 4 illustrates a helmet being used for performing a Craniocorpography (CCG) test, according to various embodiments of the present invention.

The feature and working of the present invented apparatus may be best understood by reference to figures, and especially FIGS. 3 and 4. Usually, there is a physician who will be managing and operating the apparatus.

FIG. 3 illustrates working and operational overview of the apparatus (600). Wherein, a patient (100) is wearing a helmet (101).

In various embodiments of the present invention, the helmet (101) includes a plurality of light emitting diodes (102) embedded on an outer surface (102) of the helmet (101).

In an embodiment, at least one camera (200) is positioned directionally above at a vertical distance from the helmet (101) while the helmet (101) is being worn over the head of the patient (100). In this embodiment only one camera (200) is shown. However, this should not be construed as a limitation to the present invention.

Accordingly, in one embodiment, two or more cameras were used simultaneously. The two cameras cover different portion of room to provide a wide angle view. The images from the two cameras are combined by the computer to produce one image. The advantage of using two or more cameras is to obtain wide angle coverage of the test room.

As proposed in the present apparatus, the camera (200) is a single-lens reflex camera (200), which is mounted above at a vertical distance from the location of the helmet (101) as being worn over the head of the patient (100). In another embodiment, the camera (200) is at least one of an ultra-violet light sensitive camera, a web camera, a video camera, and an infrared light sensitive camera.

Specifically, the single-lens reflex camera (200) is mounted on a ceiling (150) of a room (500) in which the Craniocorpography test is conducted. The patient (if detected with disorder) moves over a floor (600) of the Craniocorpography test room (500). The single-lens reflex camera (200) is configured with a wide-angle lens and hence adapted to capture a widened area of the Craniocorpography test room (500).

Moreover, there is a controller (400) operated by the physician to remotely control the plurality of light emitting diodes (102) of the helmet (101). As the operator (physician) is distant and not existent in front of the patient (100), there is no movement disturbance for the patient. Further, the controller (400) held by the physician is also adapted to remotely control the functioning of the single-lens reflex camera. The controlling function may be related to shutter operation, direction of the camera (200), pan, zoom, or any other relevant operation of the camera (200).

FIG. 4 illustrates a top view of the helmet (101) as proposed by the present invention. The helmet (101) includes an outer surface (102), an inner surface (not shown) and a plurality of light-emitting diodes (104, 105) embedded on the outer surface (102) of the helmet (101).

In various embodiments, the plurality of light-emitting diodes (104, 105) operates in visible range. The plurality of light-emitting diodes (104, 105) includes at least three blue light-emitting diodes (104) and at least one red light-emitting diode (104).

The at least three blue light-emitting diodes (104) are equally spaced apart from each other. The at least one red light-emitting diode (105) is placed adjacent to the one of the at least three blue light-emitting diodes.

Specifically, the at least three blue light-emitting diodes (104) are placed in a triangular pattern, wherein one of the blue light-emitting diode (104) is placed in the middle of front part (112) of the helmet (101). The other two blue light-emitting diodes (104) are placed one in the middle of the left and one in the middle of the right part of the helmet (101) respectively.

Accordingly, in such a spatial arrangement, the three blue light light-emitting diodes (104) form a triangular pattern.

The at least one red light-emitting diode (105) is placed adjacent to one of the blue light-emitting (104) placed in the middle of the front part (112) of the helmet (101).

During the operational condition, the patient (100) wears the helmet (101) and then the patient (100) is asked to step on the spot in the Craniocorpography test room (500) for a predetermined number of steps. The patient if detected with disorder moves over a floor (600) of the Craniocorpography test room (500). Usually, the patient (100) is asked to take a predetermined number of steps on the spot in the room (500) having dark environment, where the patient (100) is usually blindfolded. While performing the Craniocorpography test, the at least three blue light-emitting diodes (104) are turned on at a starting point and at a final point of the Craniocorpography test. On the other hand, the at least one red light-emitting diode (105) remains turned on throughout the operation of the Craniocorpography test. Thus the three blue light-emitting diodes (104) show the initial points and the final points of the patient movements during the Craniocorpography test. Whereas, the one red light-emitting diode (104) provides a means of showing a movement path of the patient (100).

During this movement activity, the single-lens reflex camera (200) captures the movement images of the patient (100). The single-lens reflex camera (200) provides an easy means to detect all the area of the Craniocorpography test room (500) as well as all the movement steps of the patient (100), due its wide-angle lens. The physician performing the test on the patient (100) may operate the camera (200) to ensure that the movement of the patient (100) is properly tracked. The physician may do so by providing operational control on the controller (400). The physician might additionally vary other parameters of the camera (200), like zoom, pan, focus, image intensity, and the like. The physician may also control the intensity of the LEDs using the controller (400).

Accordingly, when the Craniocorpography test is performed in either a dark room or a bright room. This is a significant advantage of the present invention.

Furthermore, there is an interface card (201) configured in conjugation with the single-lens reflex camera (200). The interface card (201) is adapted to connect the single-lens reflex camera (200) with a computing system (300) of the physician. The interface card (201) captures the patient movement data from the single-lens reflex camera (200) and transmits such received movement data to the computing device (300). In one embodiment, the interface card (201) is a network interface card, like a WiFi card, adapted to wirelessly transmit the data to the computing device (300).

The computing system (300) as provided herein is adapted to analyze and present at least a plurality of patient alignment parameters by processing the images captured by the camera (200).

In various embodiments, the computing system (300) as disclosed herein is made up a display screen, a processor, a data input terminal, a data output terminal, a data storage unit, and a data processing program. The data processing program as provided herein is specially designed to analyze and process the patient movement data using a predefined algorithm. A flowchart explaining the data processing program and the predefined algorithm is shown with reference to FIG. 6.

Figure 6:
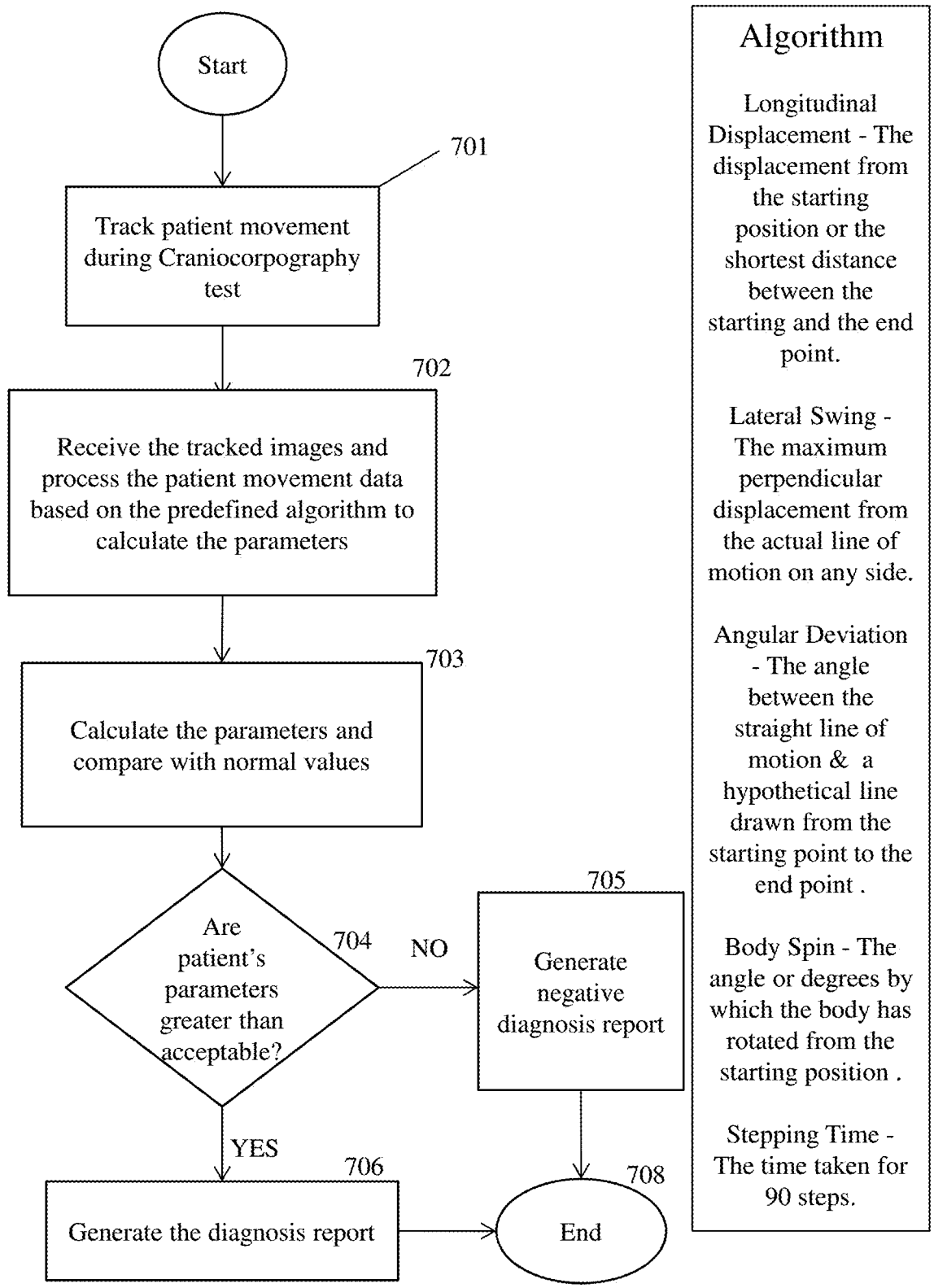
FIG. 6 illustrates a flow diagram for the data processing program for the Craniocorpography (CCG) of the present invention, according to various embodiments of the present invention.
Figure 9:
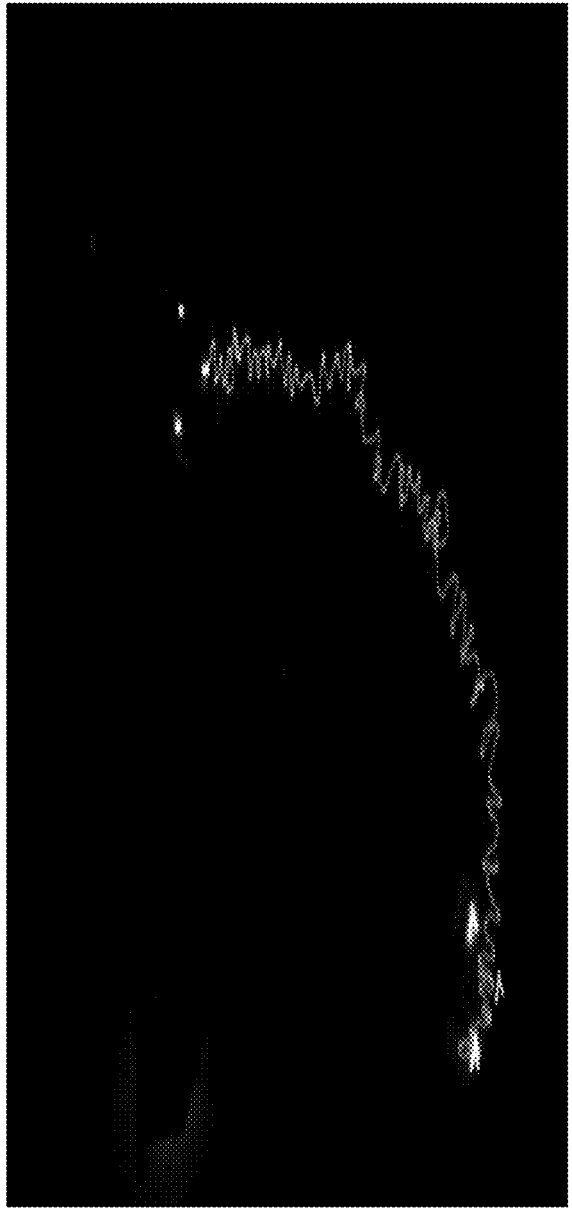
FIG. 9 illustrates a test result showing spin of the patient to the right side, using the apparatus of the present invention, according to various embodiments of the present invention.
Figure 10:
FIG. 10 illustrates a test result showing rotation of the patient to the right side, using the apparatus of the present invention, according to various embodiments of the present invention.
Figure 11:
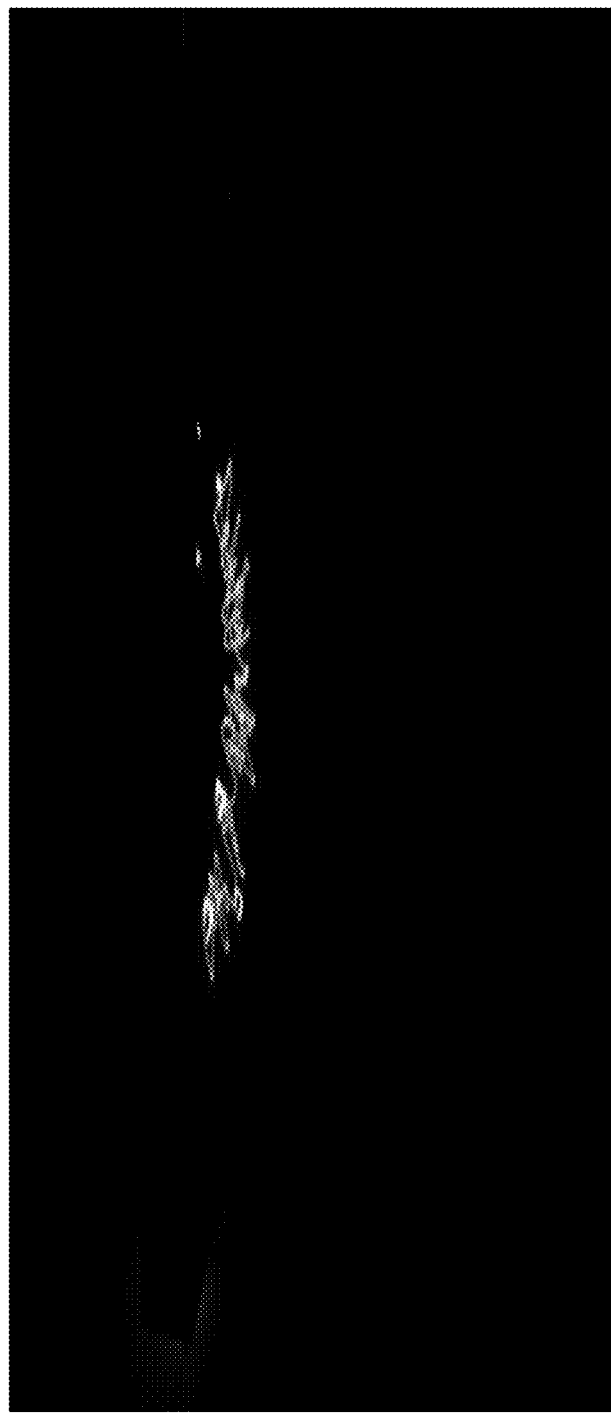
FIG. 11 illustrates test illustration for right peripheral vestibulopathy of the patient, using the apparatus of the present invention, according to various embodiments of the present invention.

As shown in FIG. 6, the data program of the computing system (300) receives various tracking images from the camera (200) of the patient (100). On receipt of the images, the data program applies a processing algorithm on these captured images.

In one embodiment, the data processing program scans the tracked images and maps it on a positional reference. The data processing program uses a pre-defined algorithm on these images to process and calculate various parameters, at step 702 and 704. For example, the data processing evaluates:—

Longitudinal Displacement—The displacement from the starting position or the shortest distance between the starting and the end point;

Lateral Swing—The maximum perpendicular displacement from the actual line of motion on any side;

Angular Deviation—The angle between the straight line of motion & a hypothetical line drawn from the starting point to the end point;

Body Spin—The angle or degrees by which the body has rotated from the starting position; and Stepping Time—The time taken for predetermined number of steps, usually 90 steps.

Thereafter, the data program generates a diagnosis report with the computed parameters listed therein, at step 706, as referred to in FIGS. 12-16. In one embodiment, the data program checks if there is a movement of the patient (100), over and above the acceptable limits, during the test. If there is no movement (over and above the acceptable limit) detected, the data program generates a report, which shows negative diagnosis, at step 705.

Figure 12:
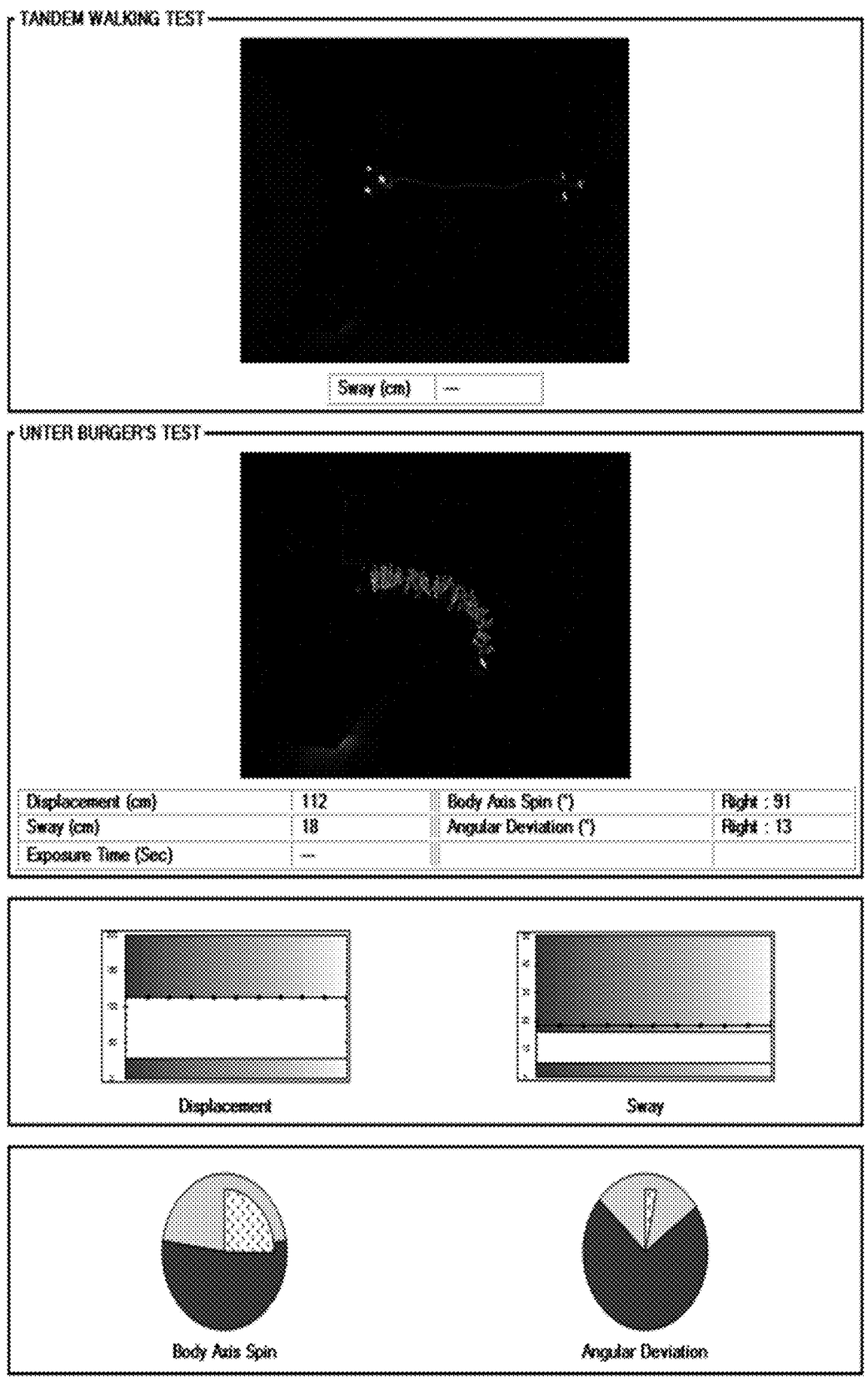

As shown in FIGS. 12-13, there is illustrated test reports automatically generated by the apparatus (600), where a patient is diagnosed with the right peripheral vestibulopathy with abnormal body axis spin.

Figure 14:
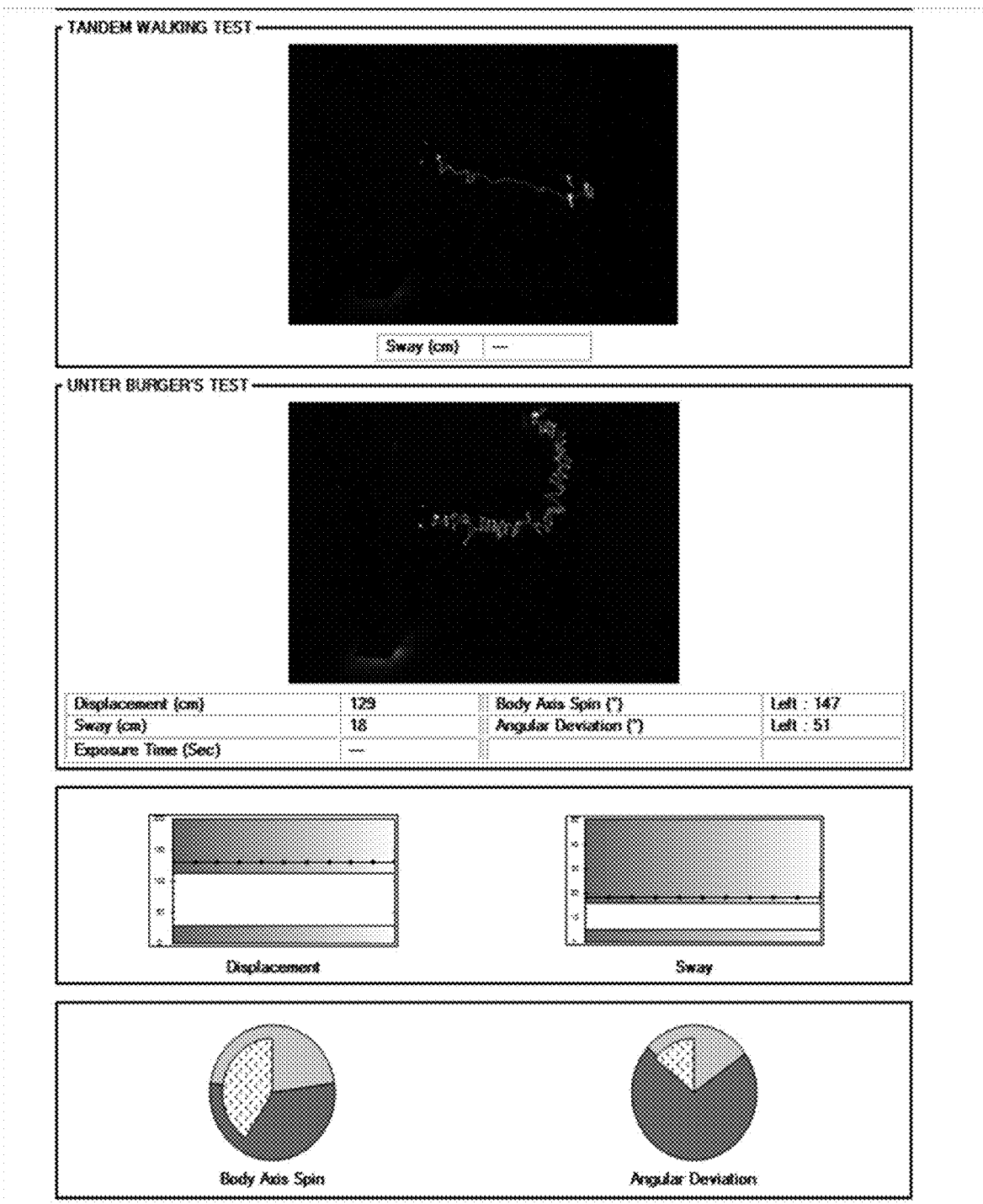

In FIG. 14, there is shown a test report automatically generated by the apparatus (600), where a patient is diagnosed with left peripheral vestibulopathy with abnormal body axis spin with increased sway.

Figure 15:
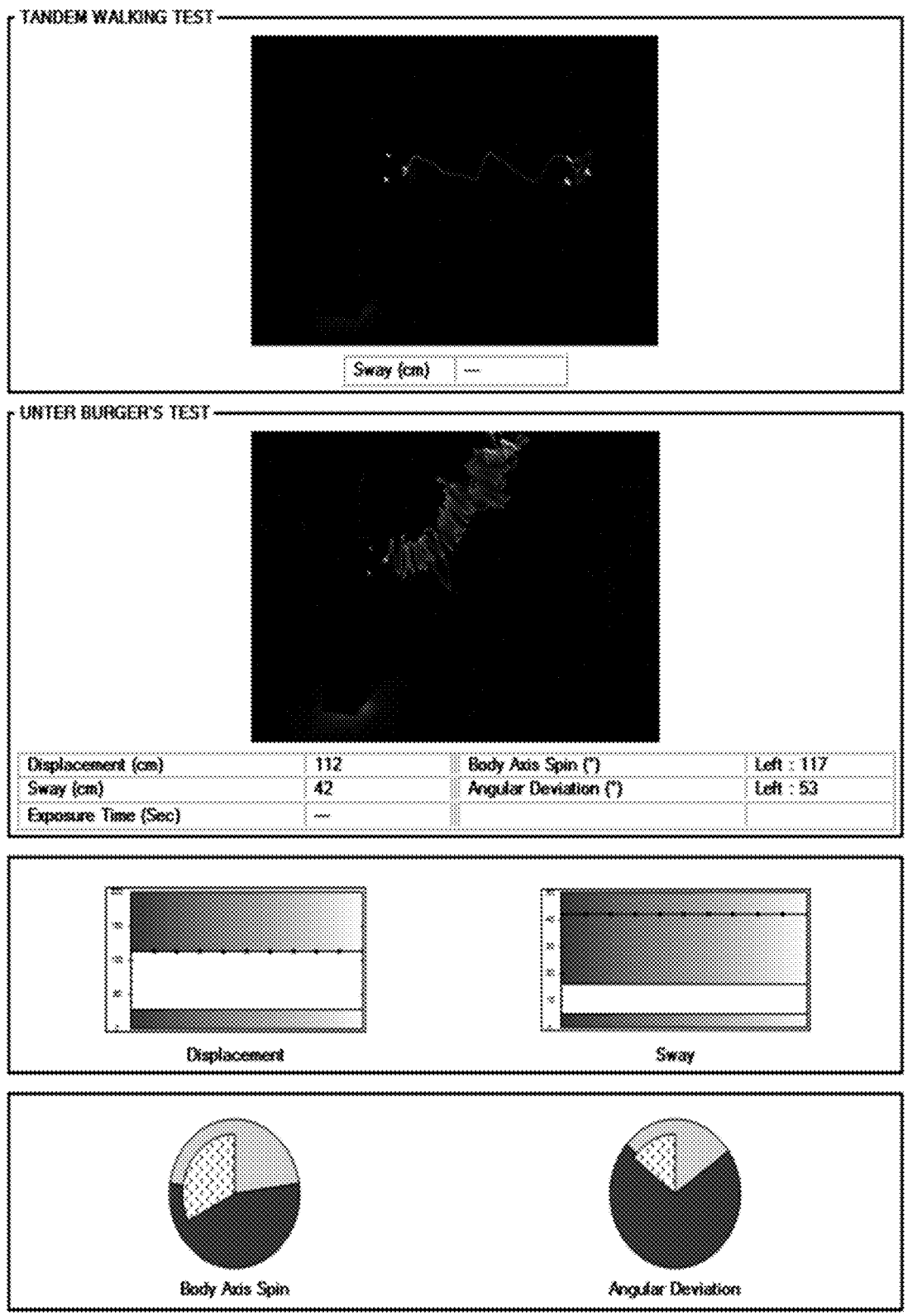

In FIG. 15, there is shown a test report automatically generated by the apparatus (600), where a patient is diagnosed with Central vestibulopathy with abnormal sway.

Figure 16:
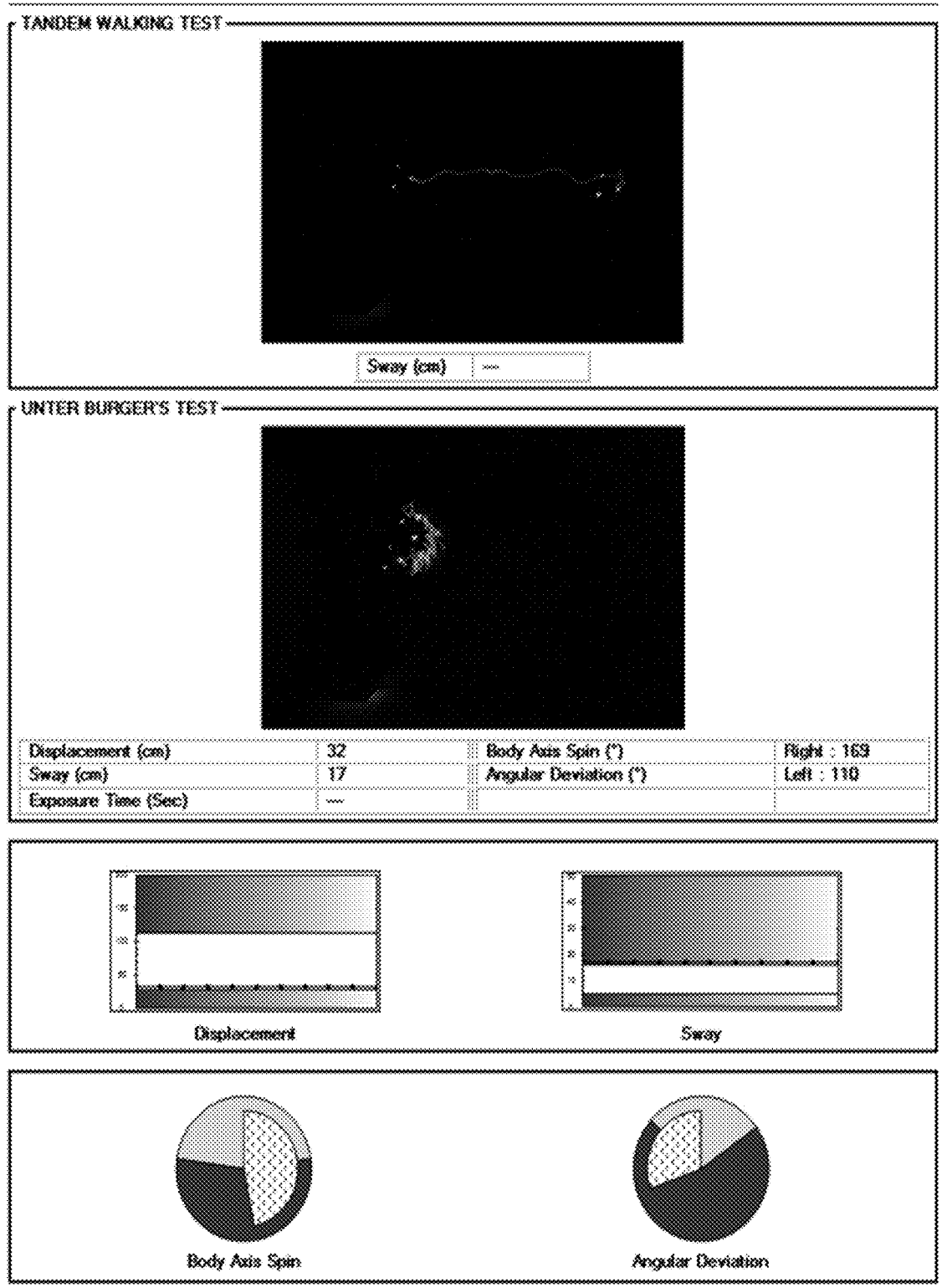

In FIG. 16, there is shown a test report automatically generated by the apparatus (600), where a patient is diagnosed with Abnormal Body axis spin & angular deviation—Meniere's disease left ear.

The plurality of patient alignment parameters as determined by the data processing program includes at least longitudinal displacement of the patient, sway of the patient, angular deviation of the patient, body axis spin of the patient and stepping time of the patient. The stepping time of the patient (100) is the actual time that the patient took to complete the ninety steps in a dark room while undergoing the Craniocorpography test. These patient alignment parameters are computed automatically, with minimum human intervention from the physician.

In a preferred embodiment, the helmet (101) is made up of a transparent material having a plurality of infrared light-emitting diodes (104, 105) embedded therein. The plurality of infrared light-emitting diodes (104, 105) is embedded in such a manner that they provide an easy means to detect the patient movement path during the Craniocorpography test condition.

Accordingly, during the Craniocorpography test the patient (100) wears the helmet (101) and then he is asked to take 90 steps on the spot. Since the patient has disorder, the patient (100) moves in a test room (500). During this movement activity an infrared camera (200) captures the movement images of the patient. The infrared camera (200) is mounted above at a vertical distance from the location of the helmet (101) as worn over the head of the patient.

The infrared camera (200) detects all the movement steps of the patient due to activity of the plurality of infrared light emitting diodes. A remote control (400) is used to turn the camera on and off and the remote control (400) is also adapted to control the plurality of light-emitting diodes. The remote control (400) ensures that the patient is not touched during the Craniocorpography test.

The arrangement of the present apparatus (600) is used to record the movement of the patient in three tasks such as Romberg test, Tandem walking and Unterburgers (Fukuda Stepping) test. Further, the apparatus (600) is adapted to analyze a plurality of balance parameters and to produce print outs of all the movement images of the patient during the test conditions.

Romberg test is generally used for the examination of the neurological functions of the person. The examination is based on the premise that a person requires at least two of the three senses to maintain balance while standing such as proprioception, vestibular function; and vision. Wherein, proprioception is the ability to know one's body in space, vestibular function is the ability to know one's head position in space; and vision is used to monitor and adjust the changes in the body position. In the Romberg test, the standing patient is asked to close his eyes and a loss of balance is interpreted as a positive Romberg's test.

Tandem walking is a method of walking or running where the toes of the back foot touch the heel of the front foot at each step. The Unterburger test is performed to determine the balance related disorder. During the Unterburger test the patient is blindfolded and asked to move on the spot for around fifty to ninety steps in a test room.

Further, the present invention discloses a method for diagnosing vertigo and balance related ailment of the patient by using Craniocorpography technique.

Figure 5:
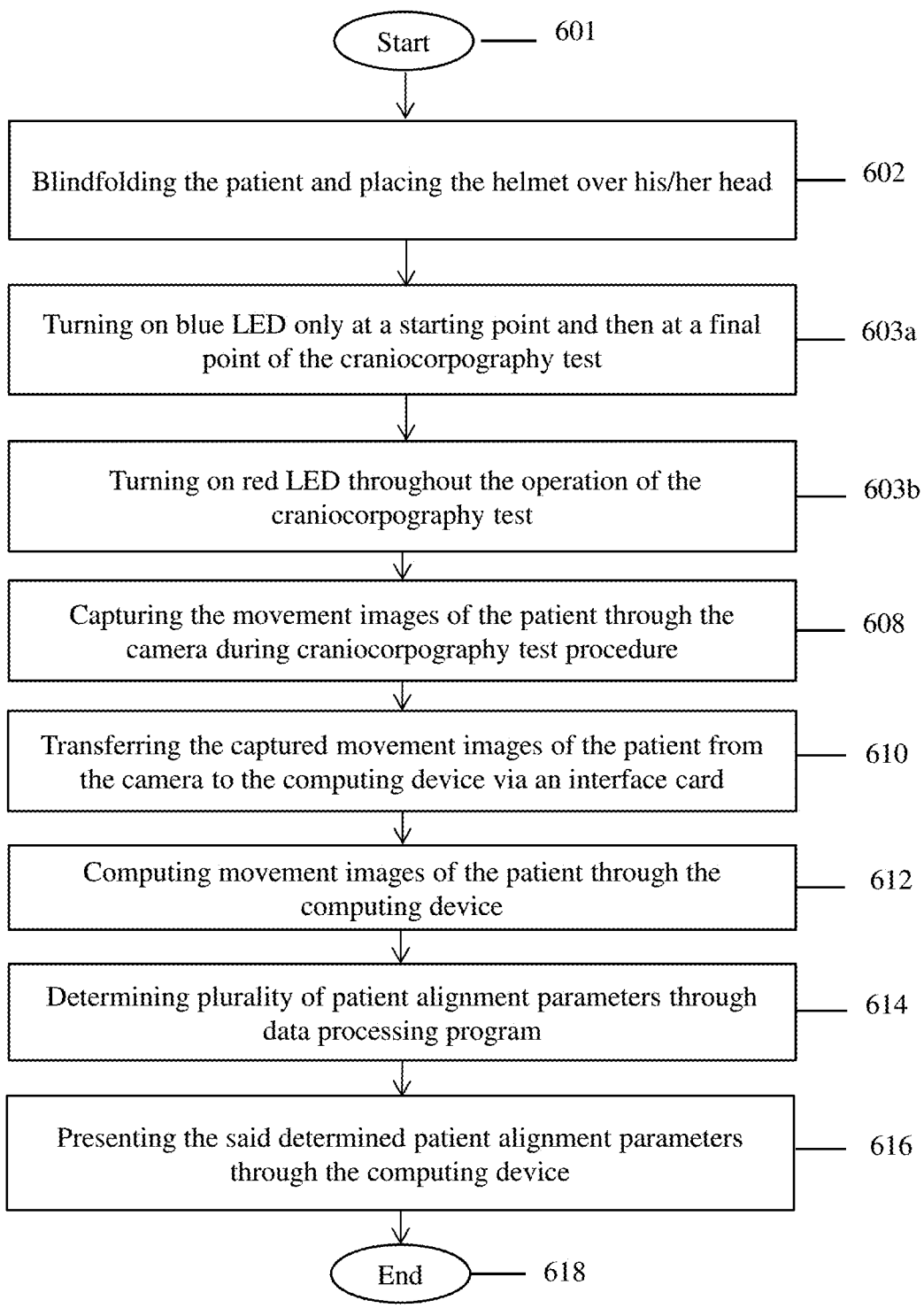
FIG. 5 illustrates a method for conducting the Craniocorpography (CCG) by using the apparatus of the present invention, according to various embodiments of the present invention.

FIG. 5 explains major test steps required for conducting the Craniocorpography test by using the apparatus (600) of the present invention. The method includes placing the helmet (101) over a head of a patient (100), as shown in step 602 of FIG. 5. The helmet (100) includes the plurality of light-emitting diodes (104, 105). Thereafter, the patient (100) is blindfolded and asked to move on the spot for around ninety steps in a test room (500). Thereafter, the method includes turning on blue LED only at a starting point and then at a final point of the craniocorpography test, at step 603a, while, the red LED is turned on throughout the operation of the Craniocorpography test, at step 603b.

The next step involves capturing movement images of the patient through the camera (200) when the patient performs the Craniocorpography technique, as shown in step 608 of FIG. 5. The camera (200) is placed directionally above at a vertical distance from the helmet (101) when being worn over the head of the patient (100).

The next step involves transferring the said captured movement images of the patient (100) from the camera (200) to the computing device (300), as shown in step 608 of FIG. 5. The transferring of said captured movement images is done through an interface card (201) which is coupled to the camera (200). Thereafter, the said captured movement images are analyzed and processed through the computing device (300), as shown in step 612 of FIG. 5.

In the next step, a plurality of patient alignment parameters is determined by using a processing program of the computing device (300), as shown in step 614 of FIG. 5. The plurality of patient alignment parameters includes at least one of a longitudinal displacement of the patient, sway of the patient, angular deviation of the patient, body axis spin of the patient and test stepping time of the patient. In the next step, the said determined patient alignment parameters are presented through the computing device (300), as shown in step 616 of FIG. 5. These patient alignment parameters are useful for diagnosing vertigo and balance related ailment of the patient.

In an embodiment, the plurality of light-emitting diodes (104, 105) is selected from at least a plurality of light-emitting diodes operable in visible range. The camera (200) is selected from at least a single lens reflex camera. In this arrangement the test room (500) is a dark test room.

In a preferred embodiment, the plurality of light-emitting diodes (104, 105) is selected from at least a plurality of light-emitting diodes (104, 105) operable in infra-red region. The camera (200) is selected from at least an infra-red light sensitive camera. In this arrangement, the test room (500) is a normal test room having sufficient lighting. This allows the physician to conduct the test on the patient (100) even in a lit up room (500).

The whole setup of the present apparatus (600) is sleek and patient friendly and thus does not give much problem during the Craniocorpography test conditions. The helmet (101) is designed to be worn by patients from all age groups. Moreover, the inbuilt battery of the helmet (101), which is powering the helmet (101), is adapted to provide energy to the plurality of light-emitting diodes of the helmet (101). Moreover, the use of blue and red colored light-emitting diodes can easily track movement of the patient.

The apparatus (600) of the present invention operates without any physical contact of the physician and the patient. The interface card (201) provides an easy means for continuously transferring the data related to the patient movements during the Craniocorpography test procedure. Further, the present apparatus (600) does not produce any disturbance to the patient while performing the Craniocorpography test. Moreover, the patient (100) does not have any external clue for maintaining his balance during the movement. Accordingly, the patient (100) has to entirely depend upon his vestibular system for maintaining his balance. Thus the accuracy for the vertigo and balance alignment parameters is very high.

Moreover, the use of the infrared light sensitive camera (200) along with infrared light emitting diodes (104, 105), as per one embodiment, provides a condition in which the Craniocorpography test procedure can be performed in the normal day light conditions. Hence, in this arrangement there is no need for a dark test room (500) and thus the patient having vertigo and balance disorders can be easily monitored by the physician. Accordingly, if the patient tends to fall during the test conditions then such accidental situation can be easily avoided.

The data processing program of the present invention is adapted to automatically calculate the test stepping time. Accordingly, there is no need for manually calculating the test stepping time (time taken to take 90 steps on the spot). Further, the data processing program is adapted to adjust the variation in the height of different patients. Moreover, the plurality of vertigo parameters is easily and accurately measured by just marking the initial position of the light-emitting diodes and then marking the final position of the light-emitting diodes. The test reports having a plurality of vertigo parameters along with the movement images are given to the patient within minutes.

The present invention should not be construed to be limited to the configuration of the method and system as described herein only. Various configurations of the system are possible which shall also lie within the scope of the present invention. It should be understood that the various components of the present invention, such as the LEDs, camera, controller, and the like, may undergo trivial modifications, which should be construed as part of the present invention.

The foregoing descriptions of specific embodiments of the present invention have been presented for purposes of illustration and description. They are not intended to be exhaustive or to limit the present invention to the precise forms disclosed, and obviously many modifications and variations are possible in light of the above teaching. The embodiments were chosen and described in order to best explain the principles of the present invention and its practical application, and to thereby enable others skilled in the art to best utilize the present invention and various embodiments with various modifications as are suited to the particular use contemplated. It is understood that various omissions and substitutions of equivalents are contemplated as circumstances may suggest or render expedient, but such omissions and substitutions are intended to cover the application or implementation without departing from the spirit or scope of the present invention.

We claim:

1. An apparatus for determining a plurality of patient alignment parameters which are used for diagnosing vertigo and balance related ailment using Craniocorpography technique, the apparatus comprising:

a helmet adapted to be worn over a head of a patient, the helmet comprising a plurality of light sources comprising at least a plurality of light-emitting diodes including at least three first light-emitting diodes having a first emitting characteristic and at least one second light-emitting diode having a second emitting characteristic different from the first emitting characteristic, such that the at least three first light-emitting diodes are equally spaced apart from each other and the at least one second light-emitting diode is placed adjacent to one of the at least three first light-emitting diodes;

at least one camera placed directionally above at a vertical distance from the helmet while the helmet is being worn over the head of the patient, the at least one camera adapted to track movement of the patient when the Craniocorpography technique is being performed on the patient;

an interface card adapted to connect to the camera, the interface card adapted to relay images captured by the camera;

a computing system in communication with the interface card, the computing system adapted to compute the plurality of patient alignment parameters processed based on the images captured by the camera; and a remote control device operatively connected to the computing system, the remote control device adapted to control the plurality of light-emitting diodes;

wherein the remote control device is configured to turn on the at least three first light-emitting diodes at a starting point and at a final point while the Craniocorpography technique is being performed on the patient and to ensure that the at least one second light-emitting diode remains on throughout the operation of the Craniocorpography technique, such that the at least one second light-emitting diode provides a means of showing the tracked path of the patient.

2. The apparatus as claimed in claim 1, wherein the plurality of light- emitting diodes is embedded on an outer surface of the helmet.

3. The apparatus as claimed in claim 2, wherein the plurality of light-emitting diodes are selected from at least a plurality of visible light-emitting diodes, a plurality of ultraviolet light-emitting diodes, and a plurality of infrared light-emitting diodes.

4. The apparatus as claimed in claim 1, wherein the camera is selected from at least a single lens reflex camera, an ultraviolet light sensitive camera, a web camera, a video camera, and an infrared light sensitive camera.

5. The apparatus as claimed in claim 2, wherein the at least three first light-emitting diodes comprise at least three blue light-emitting diodes and the at least one second light-emitting diode comprises at least one red light-emitting diode.

6. The apparatus as claimed in claim 5, wherein the at least one red light-emitting diode is placed in a front top portion of the helmet.

7. The apparatus as claimed in claim 1, wherein the computing system comprises, a data processing program, wherein the data processing program is adapted to automatically process data of the movement images of the patient.

8. The apparatus as claimed in claim 1, wherein the plurality of patient alignment parameters comprises at least one of longitudinal displacement of the patient, sway of the patient, angular deviation of the patient, body axis spin of the patient and test stepping time of the patient.

9. The apparatus as claimed in claim 1 further comprising a controller, wherein the controller is adapted to remotely control the camera.

10. The apparatus as claimed in claim 9, wherein the controller is further adapted to remotely control the plurality of light emitting diodes.

11. A method for determining a plurality of patient alignment parameters which is used for diagnosing vertigo and balance related ailment of the patient by using Craniocorpography technique, the method comprising:
placing a helmet over a head of a patient, the helmet comprising a plurality of light sources comprising at least a plurality of light-emitting diodes including at least three first light-emitting diodes having a first emitting characteristic and at least one second light-emitting diode having a second emitting characteristic different from the first emitting characteristic, such that the at least three first light-emitting diodes are equally spaced apart from each other and the at least one second light-emitting diode is placed adjacent to one of the at least three first light-emitting diodes;
turning the at least three first light-emitting diodes on at a starting point and then at a final point while the Craniocorpography technique is being performed on the patient;
turning the at least one second light-emitting diode on at the starting point and keeping the at least one second light-emitting diode on throughout the operation of the Craniocorpography technique, such that the at least one second light-emitting diode provides a means of showing a tracked path of the patient;
capturing images of the patient when the Craniocorpography technique is being performed on the patient via at least one camera placed directionally above at a vertical distance from the helmet, when being worn over the head of the patient;
transferring the said captured movement images of the patient from the camera to a computing device via an interface card coupled to the camera;
processing and analyzing the said images captured by the camera, the processing being done through the computing device;
determining the plurality of patient alignment parameters using a processing program of the computing device; and
presenting the said determined patient alignment parameters through the computing device.

12. The method as claimed in claim 11, wherein the plurality of light sources is embedded on the outer surface of the helmet.

13. The method as claimed in claim 12, wherein the plurality of light-emitting diodes are selected from at least a plurality of visible light-emitting diodes, a plurality of ultraviolet light-emitting diodes, and a plurality of infrared light-emitting diodes.

14. The method as claimed in claim 11, wherein the camera is selected from at least a single lens reflex camera, an ultraviolet light sensitive camera, video camera, web camera and an infrared camera.

15. The method as claimed in claim 11, wherein the at least three first light-emitting diodes comprise at least three blue light-emitting diodes and the at least one second light-emitting diode comprises at least one red light-emitting diode.

16. The method as claimed in claim 11 comprises controlling functionality of the camera via a remote controlling device.

17. The method as claimed in claim 16, wherein the direction of the camera is controlled by the controlling device.

18. The method as claimed in claim 16 comprises controlling intensity of the plurality of light-emitting diodes of the helmet.

19. The method as claimed in claim 11, wherein the said plurality of patient alignment parameters comprises at least longitudinal displacement of the patient, sway of the patient, angular deviation of the patient, body axis spin of the patient and test stepping time of the patient.

* * * * *